United States Patent [19]

Righelato et al.

[11] 4,234,688
[45] Nov. 18, 1980

[54] POLYSACCHARIDE PRODUCING PROCESS USING PROTEASE AND AZOTOBACTER

[75] Inventors: Renton C. Righelato; Trevor R. Jarman, both of Reading, England

[73] Assignee: Tate & Lyle Limited, London, England

[21] Appl. No.: 885,272

[22] Filed: Mar. 10, 1978

[30] Foreign Application Priority Data

Mar. 14, 1977 [GB] United Kingdom ............... 10695/77

[51] Int. Cl.$^2$ ..................... C12P 19/04; C13L 3/00; C12R 1/065
[52] U.S. Cl. .................................. 435/101; 435/274; 435/813; 435/831
[58] Field of Search ............. 195/4, 7, 31 P, 96, 195/111, 115, 13; 435/101, 274, 813, 831

[56] References Cited

U.S. PATENT DOCUMENTS

| | | | |
|---|---|---|---|
| 3,856,625 | 12/1974 | Imrie | 195/31 P |
| 3,966,618 | 6/1976 | Colegrove | 195/31 P X |
| 4,094,739 | 6/1978 | Schroeck | 195/7 |
| 4,130,461 | 12/1978 | Righelato et al. | 195/31 P |

OTHER PUBLICATIONS

Larsen, et al., "BiosynThesis of Alginate", *Carbohyd. Res.* vol. 17, (1971), pp. 287-308.

*Primary Examiner*—Thomas G. Wiseman
*Attorney, Agent, or Firm*—Ostrolenk, Faber, Gerb & Soffen

[57] ABSTRACT

The solution viscosity of a polysaccharide, microbial alginate, produced by culturing strains of *Azotobacter vinelandii*, is controlled by addition of a protease to the culture broth. The protease can be added during the culture, to obtain a polysaccharide of increased viscosity. Alternatively or additionally protease can also be added after culture but before the polysaccharide is isolated from the broth, for example, to prevent reduction of viscosity during storage. Neutral and alkaline proteases having activity at around pH 7 are particularly suitable.

9 Claims, No Drawings

POLYSACCHARIDE PRODUCING PROCESS USING PROTEASE AND AZOTOBACTER

This invention relates to the production of a microbial alginate of controlled viscosity.

Microbial alginate is a polysaccharide which can be produced by cultivation of microorganisms of the species *Azotobacter vinelandii*, for example, by the process disclosed in our British Pat. No. 1,331,771. The product is a partially acetylated variable block copolymer of 1-4 linked d-mannuronic and L-guluronic acid residues, generally with a degree of acetylation of about 20%; and, apart from the acetyl groups, it is chemically similar to alginic acid extracted from certain species of brown seaweed.

A problem which arises in the production of microbial alginate, particularly when using continuous culture conditions involving a high cell mass and high polysaccharide productivity, is that the polysaccharide solution obtained has reduced viscosity. This is believed to result from a reduction in the average molecular weight of the polysaccharide, caused by degradation by the enzyme alginate lyase—see Haug and Larsen, Carbohydrate Research, 17 (1971), 297-308. This enzyme is believed to function extracellularly; and the degradation caused can severely affect the solution viscosity, and hence the commercial utility of the polysaccharide product.

We have now found that the degradation of the polysaccharide can be controlled, and hence the viscosity of the product increased, by the incorporation of a proteolytic enzyme in the culture broth. The proteolytic enzyme can be incorporated in the culture medium on which the microorganism is grown, or added to the culture broth in some other manner during the cultivation of the microorganism, or even added to the broth after cultivation but before the polysaccharide is isolated.

In accordance with the invention, therefore, we provide a process for producing a polysaccharide by culturing a polysaccharide-producing strain of *Azotobacter vinelandii* in a nutrient medium therefor, in which process the solution viscosity of the polysaccharide produced is controlled by incorporating in the culture broth, during the culture and/or after the culture but before isolation of the polysaccharide product, a proteolytic enzyme having proteolytic activity at the pH of the culture broth.

This use of a proteolytic enzyme in a fermentation containing viable microorganisms is a surprising innovation in the field of polysaccharide production. This will be appreciated when it is considered that one known use of proteolytic enzymes, such as alkaline proteases, is in the removal of cell debris from xanthan gum solutions, produced by cultivation of strains of microorganism of the genus Xanthomonas. In that known process, microbial cells and cell fragments, which are difficult to remove from the xanthan gum solution by physical means, are degraded in situ by addition of the enzyme. However, in complete contrast to this use of proteases for the degradation of microbial cells, we have unexpectedly discovered that such an enzyme can be added to a fermentation of *A. vinelandii* in such a manner as to control the viscosity of the product without seriously affecting the viability of the microorganism. Sometimes, a slight loss in polysaccharide concentration may be experienced, as assessed by isopropanol-precipitatable matter, but this is more than offset by the increased viscosity of the product.

Different proteolytic enzymes have optimum activity at different pH values. Those which exhibit optimum activity at pH values above neutral are termed alkaline proteases, those which exhibit optimum activity at neutral pH values are termed neutral proteases, and so on. Any of these different proteolytic enzymes can, in general, be used in the process of the present invention, provided that they exhibit sufficient activity at the pH of the culture broth, which will generally be about pH 7. The proteolytic enzyme may be derived from any convenient source; but bacterial and fungal proteases are particularly useful, such as those obtainable from Novo Industri A/S of Copenhagen, Denmark, under the trade marks "Alcalase" and "Neutrase". For continuous culture, it is particularly preferred to operate at a pH of about 7.4 with a neutral or alkaline protease.

As well as being useful for increasing the viscosity of the polysaccharide produced by the culture, the proteases are also capable of stabilizing the polysaccharide in volumes of culture broth which are being stored for processing. This can be used to overcome a problem which is encountered particularly in continuous culture processes, when batches of culture broth are withdrawn from the fermenter and then stored for a considerable time before isolation of the polysaccharide, and it is then found that the viscosity of the product has fallen considerably. In accordance with this embodiment of the invention, we provide a method for producing a polysaccharide by culturing a polysaccharide-producing strain of *A. vinelandii* in a nutrient medium therefor in a fermenter, and subsequently withdrawing the culture broth from the fermenter, in which the solution viscosity of the polysaccharide produced is controlled by adding to the culture broth, after it is withdrawn from the fermenter but before isolation of the polysaccharide product, a proteolytic enzyme having proteolytic activity at the pH of the broth. In this way, the actual culture may be carried out in the absence of the enzyme, or at low enzyme levels, and then the level of proteolytic enzyme in the culture broth can be raised before storage.

The level of proteolytic enzyme used in any of the embodiments of the invention will, of course, depend on the degree of viscosity control required and the relative activity of the enzyme. Also, whereas unduly high enzyme levels should be avoided during cultivation of the microorganism, to avoid any risk of impairing the viability of the microorganism cells, higher levels can be used when the enzyme is added after the culture, for instance, to broth withdrawn for storage, since the viability of the microorganism is then no longer important. In general, it is preferred to use the proteolytic enzyme at a level of from 0.005 to 1.0 Anson units per liter of broth; and a range of from 0.005 to 0.5 Anson units per liter is more highly preferred for use during the culture of the microorganism. (The Anson unit is defined as that amount of enzyme which will release 1 milliequivalent of tyrosine per minute from denatured haemaglobin at 30° C. and pH 7.5).

The following examples illustrate the invention further:

EXAMPLE 1

This Example illustrates the increase in the solution viscosity of the polysaccharide product obtained from continuous cultures of *Azotobacter vinelandii* on the addition of protease to the culture.

Three 2 l continuous cultures of *Azotobacter vinelandii* MCIB 9068 were established using a culture medium containing:

| | |
|---|---|
| Sucrose | 60 g/l |
| $KH_2PO_4$ | 0.064 g/l |
| $K_2HPO_4$ | 0.26 g/l |
| $MgSO_4 7H_2O$ | 1.6 g/l |
| NaCl | 1.6 g/l |
| $Na_2MoO_4$ | 0.008 g/l |
| $CaCl_2 2H_2O$ | 0.34 g/l |
| $FeCl_2 4H_2O$ | 0.017 g/l |

Air was supplied to the stirred culture at 1.4 l/min. the temperature was 36° C., the addition rate was 0.13 $h^{-1}$; and the pH was 7.4 (controlled by the automatic addition of 1 M NaOH). Foaming was controlled by the addition of a silicone anti-foaming agent. Under these conditions the specific respiration rate of the organism was in the range 20–30 m.mol $O_2$/h/g cell.

The concentration of isopropanol-precipitatable matter in the culture broth was determined as follows: A sample of culture broth (25 ml) was added to isopropanol (75 ml), the mixture shaken and the precipitate obtained collected by filtration through a preweighed glass fibre filter disc. The disc plus precipitate was dried to constant weight in vacuo at 45° C.

The consistency index of the culture broth was determined by measurement of the apparent viscosity of the culture broth at a range of shear rates between 1 $sec^{-1}$ and 1000 $sec^{-1}$ using a Wells-Brookfield model LVT, or Model HBT, cone and plate viscometer. The logarithm of the apparent viscosity was then plotted against the logarithm of the shear rate and the plot obtained was extrapolated to determine the consistency index (i.e. the apparent viscosity at a shear rate or 1 $sec^{-1}$).

Following the addition of a protease preparation (Neutrase, 3 Anson units/g, supplied by Novo Industri A/S, Copenhagen, Denmark) to final concentrations of 0.006 g/l and 0.012 g/l in two of the three culture broths (these concentrations being subsequently maintained by the further addition of the protease in the inflowing culture medium), a marked increase in the culture viscosity occurred in these broths although the concentration of isopropanol-precipitatable matter decreased.

Samples of culture broth were removed after 6 residence times (2 days), sodium chloride was added to a final concentration of 0.1 M and the bacterial cells were removed by centrifugation at 25,000 G for 40 minutes. The sediment obtained was resuspended in distilled water, recentrifuged and dried at 105° C. to constant weight for cell mass determination. The supernatant obtained from the first centrifugation was added to isopropanol (3 volumes) and the precipitated polysaccharide was collected and freeze dried. A 1% (w/v) solution of the freezedried, cell-free polysaccharide was prepared and the consistency index of the solution determined.

The results are given in the following table (Table 1)

TABLE 1

| Neutrase (mg/l) | Cell mass (g/l) | Polysaccharide produced (g/l) | Consistency index of culture (cp) | Consistency index of a 1% solution of cell-free polysaccharide (cp) |
|---|---|---|---|---|
| 0 | 4.1 | 10.9 | 18 | 23.5 |
| 6 | 3.5 | 8.6 | 85 | 76 |
| 12 | 3.1 | 6.2 | 2500 | 2030 |

EXAMPLE 2

Two continuous cultures of an *Azotobacter vinelandii* strain derived from *Azotobacter vinelandii* NCIB 9068 were established using the culture medium and conditions described in Example 1. To one culture the protease preparation Alcalase (supplied by Novo Industri A/S, 1.5 Anson units/g) was added to a final concentration of 6 mg/l whereas no protease was added to the other culture. In the steady state conditions which were established, the culture viscosity of the protease-treated culture was higher than the (non-protease-treated) control but the polysaccharide concentration of the cultures was similar. In addition, the viscosity of solutions of the cell-free polysaccharide obtained from the protease-treated culture was higher than the control (Table 2).

TABLE 2

| Alcalase (mg/l) | Cell mass (g/l) | Polysaccharide produced (g/l) | Consistency index of culture (cp) | Consistency index of a 1% solution of cell-free polysaccharide (cp) |
|---|---|---|---|---|
| 0 | 4.4 | 17.6 | 30 | 23 |
| 6 | 3.9 | 18.4 | 1100 | 780 |

EXAMPLE 3

A similar experiment was carried out using Alcalase (supplied by Novo Industri A/S; 6 Anson units/g) at a level of 0.01 g/l measuring the consistency index and the content of 4,5-unsaturated uronic acid of cell-free polysaccharide before and after enzyme addition.

The 4,5-unsaturated uronic acid product of alginate lyase activity was estimated using the periodate-thiobarbituric acid assay as described by Weissbach, A and Hurwitz J (Journal of Biological Chemistry, 234 (1958) 705–709): 0.01 μmole of 4,5-unsaturated uronic acid was taken to produce an extinction of 0.29 at a wavelength of 549 nm (Press and Ashwell, Journal of Biological Chemistry, 237 (1962) 309–316) and using this standard, the content of 4, 5-unsaturated uronic acid residues was determined and was expressed as a percentage of the total uronic acid residues. The results are shown in Table 3 below.

TABLE 3

| Sample | Consistency index of a 1% solution of cell-free polysaccharide (cp) | Content of 4,5-unsaturated uronic acid (as % of total uronic acid) |
|---|---|---|
| 1. Before Alcalase addition | 4.6 | 0.38 |
| 2. After Alcalase | $2.5 \times 10^3$ | 0.02 |

TABLE 3-continued

| Sample | Consistency index of a 1% solution of cell-free polysaccharide (cp) | Content of 4,5-unsaturated uronic acid (as % of total uronic acid) |
| --- | --- | --- |
| addition | | |

The sample of cell-free polysaccharide, obtained after protease addition to the culture, gave solutions with very much greater viscosity than the sample taken before protease addition. It is clear that protease enables a product of high viscosity to be obtained. The decreased content of the 4,5-unsaturated uronic acid, which is produced by the action of alginate lyase in Sample 2, provides evidence that the protease is controlling the degradation of the polysaccharide by alginate lyase. A polymer of higher solution viscosity is therefore obtained.

EXAMPLE 4

This Example illustrates the increase in the viscosity of the polysaccharide product obtained from batch cultures of *Azotobacter vinelandii*, grown in the presence of a protease.

*Azotobacter vinelandii* NCIB 9068 was grown in batch culture in aerated, stirred tank fermenters containing 8 l of a medium containing:

| | |
| --- | --- |
| Sucrose | 40 g/l |
| $KH_2PO_4$ | 0.064 g/l |
| $K_2HPO_4$ | 0.25 g/l |
| $MgSO_4 7H_2O$ | 0.4 g/l |
| NaCl | 0.2 g/l |
| $Na_2MoO_4$ | 0.008 g/l |
| $CaCl_2 2H_2O$ | 0.024 g/l |
| $FeCl_2 4H_2O$ | 0.068 g/l |

To two such fermenters Alcalase (1.5 Anson units/g) was added to a final concentration of 0.1 g/l and 0.01 g/l respectively, whilst an identical culture with no protease added acted as the control experiment. Fermentation parameters were: temperature, 36° C.; pH 7.4, controlled by the automatic addition of 2 M NaOH; and air flow rate 4 l/min. Foaming was controlled by addition of a silicone anti-foaming agent. The impeller speed, which was initially 350 rpm, was increased throughout the fermentation so as to maintain the specific respiration rate of the organism in the range 6–14 m.mol $O_2$/h/g cell.

Fermentation was commenced by the addition of 160 ml of a shake-flask culture of the organism, and continued for 40 h. After 40 h, the isopropanol-precipitatable matter of the culture broth was determined, a cell-free sample of the polysaccharide produced was obtained, and the consistency index of a 1% (w/v) solution of this sample was determined (Table 4).

TABLE 4

| | Isopropanol-precipitatable matter (g/l) | Consistency index of a 1% solution of cell-free polysaccharide (cp) |
| --- | --- | --- |
| Culture 1. No Alcalase added | 7.5 | 22 |
| Culture 2. 0.01 g/l Alcalase added | 6.6 | 46 |
| Culture 3. | 5.9 | 500 |

TABLE 4-continued

| | Isopropanol-precipitatable matter (g/l) | Consistency index of a 1% solution of cell-free polysaccharide (cp) |
| --- | --- | --- |
| 0.1 g/l Alcalase added | | |

EXAMPLE 5

This Example demonstrates the stabilization of the viscosity of *Azotobacter vinelandii* culture broths on storage in the presence of a protease.

To samples of fermentation broth (20 ml) from a polysaccharide-producing continuous culture of *Azotobacter vinelandii* NCIB 9068 was added a solution of Alcalase (6 Anson units/g) (0.2 ml) to give a final concentration of Alcalase of 0.1 g/l. An equal volume of water was added to other samples which acted as untreated controls. The samples were incubated at 30° C. and the apparent viscosity at a shear rate of 46 $sec^{-1}$ was periodically measured on a Wells-Brookfield Model LVT cone and plate viscometer. The apparent viscosity of the protease-treated broth remain in the same range throughout the experiment, whereas that of the untreated broth fell significantly (Table 5).

TABLE 5

| Apparent viscosity at shear rate of 46 $sec^{-1}$ | Time (hours) | | | | |
| --- | --- | --- | --- | --- | --- |
| | 0 | 1 | 2 | 3 | 4½ |
| Protease-treated broth | 39 | 35 | 37 | 38 | 40 |
| Untreated broth | 46 | 26 | 20 | 18 | 17 |

We claim:

1. In a process for producing a polysaccharide by culturing a polysaccharide-producing strain of *Azotobacter vinelandii* in a culture broth containing a nutrient medium for said strain, the improvement which comprises regulating the solution viscosity of the polysaccharide product by incorporating in the culture broth during the culture a viscosity regulating effective amount of a protease having proteolytic activity at the pH of the culture broth.

2. The process of claim 1, wherein the protease is incorporated at a level of from 0.005 to 1.0 Anson units per liter of culture broth.

3. The process of claim 1, wherein the protease is incorporated during the culture of the said strain at a level of from 0.005 to 0.5 Anson units per liter of broth.

4. The process of claim 1, wherein additional protease is incorporated in said broth after the culture of the said strain.

5. The process of claim 1, wherein the culture is performed as a continuous fermentation at a pH of about 7.4 and the protease is a neutral or alkaline protease.

6. In a process for producing a polysaccharide by culturing in a fermenter polysaccharide-producing strain of *Azotobacter vinelandii* in a culture broth containing a nutrient medium for said strain, and subsequently withdrawing the culture broth from the fermenter and storing the broth for a finite period before isolation of the polysaccharide product from the broth, the improvement which comprises conducting said culturing in the presence of a first amount of a protease having proteolytic activity at the pH of the culture broth and by adding to the culture broth, after it is withdrawn from the fermenter but before isolation of the polysaccharide product therefrom, second amount of said protease, said first and second amounts together being a solution viscosity regulating amount whereby the solution viscosity of the polysaccharide product is regulated.

7. The process of claim 6, wherein the protease is incorporated at a level of from 0.005 to 1.0 Anson units per liter of culture broth.

8. The process of claim 6, wherein the protease is incorporated at a level of from 0.005 to 0.5 Anson units per liter of broth.

9. The process of claim 6, wherein the culture is performed as a continuous fermentation at a pH of about 7.4 and the protease is a natural or alkaline protease.

* * * * *